(12) United States Patent
Leung et al.

(10) Patent No.: US 7,868,181 B2
(45) Date of Patent: Jan. 11, 2011

(54) COMPOUNDS

(75) Inventors: Carmen Leung, Montreal (CA);
Miroslaw Tomaszewski, Montreal (CA);
Simon Woo, Montreal (CA)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/274,837

(22) Filed: Nov. 20, 2008

(65) Prior Publication Data
US 2009/0137650 A1 May 28, 2009

Related U.S. Application Data

(63) Continuation of application No. 11/671,153, filed on Feb. 5, 2007, now abandoned.

(51) Int. Cl.
*A61K 31/4188* (2006.01)
*C07D 487/10* (2006.01)
(52) U.S. Cl. .................................. 548/301.1; 514/389
(58) Field of Classification Search ............... 548/301.1
See application file for complete search history.

(56) References Cited

U.S. PATENT DOCUMENTS

| 4,611,062 | A | * | 9/1986 | Bedford et al. | .......... | 548/301.1 |
| 2009/0076049 | A1 | | 3/2009 | Horoszok et al. | | |

FOREIGN PATENT DOCUMENTS

| EP | 28906 | | 10/1980 |
| EP | 66378 | | 5/1982 |
| EP | 066378 | A1 * | 12/1982 |
| EP | 115679 | | 10/1987 |
| WO | 9207830 | | 5/1992 |
| WO | 0105790 | | 1/2001 |
| WO | 2004049601 | | 6/2004 |
| WO | 2004087658 | | 10/2004 |
| WO | 2004100865 | | 11/2004 |
| WO | 2004110986 | | 12/2004 |
| WO | 2006007851 | | 1/2006 |

OTHER PUBLICATIONS

Caterina, M.J., Schumacher, M.A., et.al., Nature (1997) v. 389 p. 816-824.
Tominaga, M., Caterina, M.J. et.al. Neuron (1998) v. 21, p. 531-543.
Walker et al J Pharmacol Exp Ther. Jan. 2003; 304(1):56-62.
Rashid et al J Pharmacol Exp Ther. Mar. 2003; 304(3):940-948.
Hwang and Oh Curr Opin Pharmacol Jun. 2002; 2(3):235-242.
Yiangou et al BJU Int Jun. 2001; 87(9):774-779.
Szallasi Am J Clin Pathol (2002) 118: 110-121.
Golub, et al. Science, vol. 286, Oct. 15, 1999, pp. 531-537.

* cited by examiner

*Primary Examiner*—Laura L. Stockton
(74) *Attorney, Agent, or Firm*—Karen Kondrad

(57) ABSTRACT

The present invention relates to new compounds of formula I,

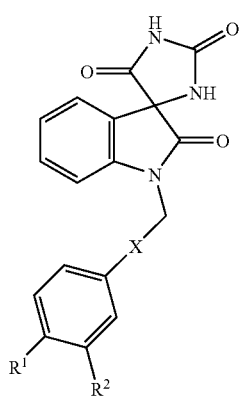

where $R^1$ and $R^2$ are independently halo or $C_{1-3}$ haloalkyl,
X is ethenyl or ethynyl,
or a salt thereof.

1 Claim, No Drawings

COMPOUNDS

This application is a continuation of U.S. patent application Ser. No. 11/671,153 which was filed on Feb. 5, 2007 now abandoned, which is hereby incorporated by reference.

FIELD OF THE INVENTION

The present invention relates to new compounds, to pharmaceutical formulations containing said compounds and to the use of said compounds in therapy. The present invention further relates to processes for the preparation of said compounds and to the use of intermediates in the preparation thereof.

BACKGROUND OF THE INVENTION

Pain sensation in mammals is due to the activation of the peripheral terminals of a specialized population of sensory neurons known as nociceptors. Capsaicin, the active ingredient in hot peppers, produces sustained activation of nociceptors and also produces a dose-dependent pain sensation in humans. Cloning of the vanilloid receptor 1 (VR1 or TRPV1) demonstrated that VR1 is the molecular target for capsaicin and its analogues. (Caterina, M. J., Schumacher, M. A., et. al. Nature (1997) v. 389 p 816-824). Functional studies using VR1 indicate that it is also activated by noxious heat, tissue acidification and other inflammatory mediators (Tominaga, M., Caterina, M. J. et. al. Neuron (1998) v. 21, p. 531-543). Expression of VR1 is also regulated after peripheral nerve damage of the type that leads to neuropathic pain. These properties of VR1 make it a highly relevant target for pain and for diseases involving inflammation. While agonists of the VR1 receptor can act as analgesics through nociceptor destruction, the use of agonists, such as capsaicin and its analogues, is limited due to their pungency, neurotoxicity and induction of hypothermia. Instead, agents that block the activity of VR1 should prove more useful. Antagonists would maintain the analgesic properties, but avoid pungency and neurotoxicity side effects.

Compounds with VR1 inhibitor activity are believed to be of potential use for the treatment and/or prophylaxis of disorders such as pain, especially that of inflammatory or traumatic origin such as arthritis, ischaemia, cancer, fibromyalgia, low back pain and post-operative pain (Walker et al J Pharmacol Exp Ther. (2003) January; 304(1):56-62). In addition to this visceral pains such as chronic pelvic pain, cystitis, irritable bowel syndrome (IBS), pancreatitis and the like, as well as neuropathic pain such as sciatia, HIV neuropathy, multiple sclerosis, and the like (Walker et al ibid, Rashid et al J Pharmacol Exp Ther. (2003) March; 304(3):940-8), are potential pain states that could be treated with VR1 inhibiton. These compounds are also believed to be potentially useful for inflammatory disorders like asthma, cough, inflammatory bowel disease (IBD) (Hwang and Oh Curr Opin Pharmacol (2002) June; 2(3):235-42). Compounds with VR1 blocker activity are also useful for itch and skin diseases like psoriasis and for gastro-esophageal reflux disease (GERD), emesis, cancer, urinary incontinence and hyperactive bladder (Yiangou et al BJU Int (2001) June; 87(9):774-9, Szallasi Am J Clin Pathol (2002) 118: 110-21). VR1 inhibitors are also of potential use for the treatment and/or prophylaxis of the effects of exposure to VR1 activators like capsaicin or tear gas, acids or heat (Szallasi ibid).

A further potential use relates to the treatment of tolerance to VR1 activators.

VR1 inhibitors may also be useful in the treatment of interstitial cystitis and pain related to interstitial cystitis.

VR1 inhibitors may also be useful in the treatment of obesity and migraine; WO2006/007851 discloses the use of VR1 antagonists for the treatment of obesity.

EP 66378 and EP 28906 disclose spiro-hydantoin derivatives for use as inhibitors of aldose reductase.

WO 92/07830 describes spiro-hydantoin derivatives and their use as antagonists for gastrin releasing peptide.

DETAILED DESCRIPTION OF THE INVENTION

The object of the present invention is to provide compounds of said kind which exhibit inhibitory activity at the vanilloid receptor 1 (VR1), along with good Drug Metabolism and Pharmacokinetics (DMPK) properties.

A further object is to provide such compounds that exhibit improved potency in-vitro, improved selectivity, and improved solubility.

Accordingly, the present invention provides compounds of formula I,

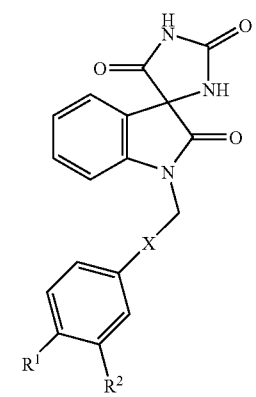

I where $R^1$ and $R^2$ are independently halo or $C_{1-3}$haloalkyl,

X is ethenyl or ethynyl, or a salt thereof, with the proviso that it is not 1'-[(2E)-3-(3,4-dichlorophenyl)prop-2-en-1-yl]-2H,5H-spiro[imidazolidine-4,3'-indole]-2,2',5(1'H)-trione in racemic form.

One embodiment of the invention relates to a compound of formula I wherein $R^1$ is halo and $R^2$ is $C_{1-3}$haloalkyl.

Another embodiment of the invention relates to a compound of formula I wherein $R^1$ is chloro or fluoro and $R^2$ is $C_{1-3}$chloroalkyl or $C_{1-3}$fluoroalkyl.

A further embodiment of the invention relates to a compound of formula I wherein $R^1$ is chloro.

One embodiment of the invention relates to a compound of formula I wherein $R^1$ and $R^2$ are chloro.

Another embodiment of the invention relates to a compound of formula I wherein X is

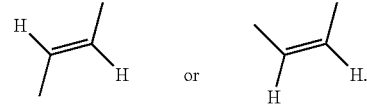

A further embodiment of the invention relates to a compound of formula I wherein X is ethynyl.

One embodiment of the invention relates to a compound of formula I selected from the group consisting of
1'-[(2E)-3-(3-chloro-4-trifluorophenyl)prop-2-en-1-yl]-2H,5H-spiro[imidazolidine-4,3'-indole]-2,2',5(1'H)-trione
and
1'-[3-(3,4-dichlorophenyl)prop-2-yn-1-yl]-2H,5H-spiro[imidazolidine-4,3'-indole]-2,2',5(1'H)-trione.

Another embodiment of the invention relates to a compound of formula I for use as a medicament, with the proviso that the compound is not 1'-[(2E)-3-(3,4-dichlorophenyl)prop-2-en-1-yl]-2H,5H-spiro[imidazolidine-4,3'-indole]-2,2',5(1'H)-trione in racemic form.

A further embodiment of the invention relates to a compound of formula I

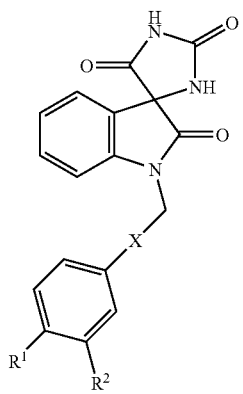

I where $R^1$ and $R^2$ are independently halo or $C_{1-3}$haloalkyl,

X is ethenyl or ethynyl, or a salt thereof, for use as a medicament for treatment of VR1 mediated disorders.

One embodiment of the invention relates to use of a compound having the formula I

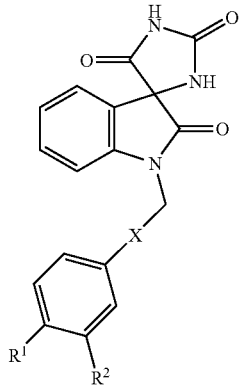

I where $R^1$ and $R^2$ are independently halo or $C_{1-3}$haloalkyl,

X is ethenyl or ethynyl, or a salt thereof, in the manufacture of a medicament, with the proviso that the compound is not 1'-[(2E)-3-(3,4-dichlorophenyl)prop-2-en-1-yl]-2H,5H-spiro[imidazolidine-4,3'-indole]-2,2',5(1'H)-trione in racemic form; in one embodiment this use is for treatment of VR1 mediated disorders.

Another embodiment of the invention relates to use of a compound having the formula I

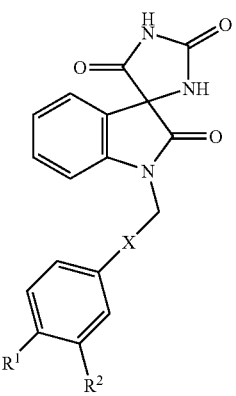

I where $R^1$ and $R^2$ are independently halo or $C_{1-3}$haloalkyl,

X is ethenyl or ethynyl, or a salt thereof, in the manufacture of a medicament for treatment of VR1 mediated disorders.

The present invention also provides a substantially pure single enantiomer having the formula II:

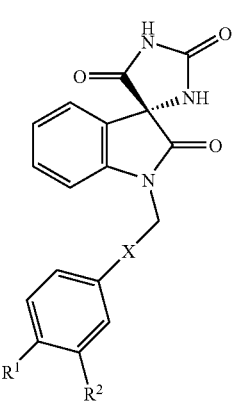

II where $R^1$ and $R^2$ are independently halo or $C_{1-3}$haloalkyl,

X is ethenyl or ethynyl, or a salt thereof.

One embodiment of the invention relates to an enantiomer of formula II wherein $R^1$ is halo and $R^2$ is $C_{1-3}$haloalkyl.

Another embodiment of the invention relates to an enantiomer of formula II wherein $R^1$ is chloro or fluoro and $R^2$ is $C_{1-3}$chloroalkyl or $C_{1-3}$fluoroalkyl.

A further embodiment of the invention relates to an enantiomer of formula II wherein $R^1$ is chloro.

One embodiment of the invention relates to an enantiomer of formula II wherein $R^1$ and $R^2$ are chloro.

Another embodiment of the invention relates to an enantiomer of formula II wherein X is

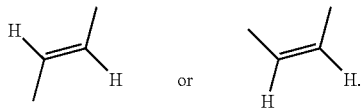

A further embodiment of the invention relates to an enantiomer of formula II wherein X is ethynyl.

One embodiment of the invention relates to an enantiomer of formula II selected from the group consisting of
(4R)-1'-[(2E)-3-(3,4-dichlorophenyl)prop-2-en-1-yl]-2H,5H-spiro[imidazolidine-4,3'-indole]-2,2',5(1'H)-trione,
(4R)-1'-[(2E)-3-(3-chloro-4-trifluorophenyl)prop-2-en-1-yl]-2H,5H-spiro[imidazolidine-4,3'-indole]-2,2',5(1'H)-trione, and
(4R)-1'-[3-(3,4-dichlorophenyl)prop-2-yn-1-yl]-2H,5H-spiro[imidazolidine-4,3'-indole]-2,2',5(1'H)-trione.

Listed below are definitions of various terms used in the specification and claims to describe the present invention.

For the avoidance of doubt it is to be understood that where in this specification a group is qualified by 'hereinbefore defined', 'defined hereinbefore' or 'defined above' the said group encompasses the first occurring and broadest definition as well as each and all of the other definitions for that group.

Unless specified otherwise within this specification, the nomenclature used in this specification generally follows the examples and rules stated in *Nomenclature of Organic Chemistry, Sections A, B, C, D, E, F, and H*, Pergamon Press, Oxford, 1979, which is incorporated by references herein for its exemplary chemical structure names and rules on naming chemical structures.

For the avoidance of doubt it is to be understood that in this specification "$C_{1-3}$" means a carbon group having 1, 2, or 3 carbon atoms.

In this specification, unless stated otherwise, the term "alkyl" includes both straight and branched chain alkyl groups and may be, but are not limited to methyl, ethyl, n-propyl, i-propyl, n-butyl, i-butyl, s-butyl, t-butyl, n-pentyl, i-pentyl, t-pentyl, neo-pentyl, n-hexyl or i-hexyl, t-hexyl.

As depicted in this specification

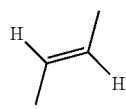

represents a trans-ethenyl group and

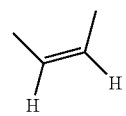

represents a cis-ethenyl group.

In this specification, unless stated otherwise, the term "halo" and "halogen" may be fluoro, iodo, chloro or bromo.

The term "haloalkyl" denotes an alkyl group wherein the alkyl is substituted with halogen ranging from one to fully substituted, wherein a fully substituted haloalkyl can be represented by the formula $C_hL_{2h+1}$ wherein L is a halogen and "h" represents the number of carbon atoms; when more than one halogen is present then the halogens may be the same or different and selected from the group consisting of F, Cl, Br and I; it is understood that the terms "alkyl" and "halogen" have the same definition as found herein. In some embodiments, haloalkyl is a "$C_{1-3}$ haloalkyl" and the group contains 1 to 3 carbons, some embodiments contain 1 to 2 carbons, and some embodiments contain 1 carbon. When the haloalkyl is fully substituted with halogen atoms, this group is referred herein as a perhaloalkyl; one example is an alkyl fully substituted with fluorine atoms and is referred to herein as a "perfluoroalkyl." In some embodiments, examples of a haloalkyl include, but is not limited to, difluoromethyl, fluoromethyl, 2,2,2-trifluoroethyl, 2,2-difluoroethyl, 2-fluoroethyl, 1,2,2-trifluoroethyl, 1,2-difluoroethyl, 1,1-difluoroethyl, 1,1,2-trifluoroethyl, 3,3,3-trifluoropropyl, 2,2-difluoropropyl, 3,3-difluoropropyl, 3-fluoropropyl, 2,3,3-trifluoropropyl, 2,3-difluoropropyl, 2,2,3,3,3-pentafluoropropyl, 2,2,3,3-tetrafluoropropyl, 2,2,3-trifluoropropyl, 1,2,3,3-tetrafluoropropyl, 1,2,3-trifluoropropyl, 3,3-difluoropropyl, 1,2,2,3-tetrafluoropropyl, 4,4-difluorobutyl, 3,3-difluorobutyl, 4,4,4-trifluorobutyl, 3,3-difluorobutyl, and the like. In some embodiments, examples of a perfluoroalkyl include, but not limited to, trifluoromethyl, pentafluoroethyl, heptafluoropropyl, 1,2,2,2-tetrafluoro-1-trifluoromethyl-ethyl, and the like. In one embodiment the term "$C_{1-3}$haloalkyl" may include, but is not limited to fluoromethyl, difluoromethyl, trifluoromethyl, fluoroethyl, difluoroethyl or bromopropyl.

The present invention relates to the compounds of formula I and the enantiomers of formula II as hereinbefore defined as well as to the salts thereof. Salts for use in pharmaceutical formulations will be pharmaceutically acceptable salts, but other salts may be useful in the production of the compounds of formula I and/or the enantiomers of formula II.

A suitable pharmaceutically acceptable salt of the compounds and enantiomers of the invention is, for example, an acid or base addition salt, for example a salt with an inorganic or organic base or acid. In addition, a suitable pharmaceutically acceptable salt of the compounds and enantiomers of the invention is an alkali metal salt, an alkaline earth metal salt or a salt with an organic base.

Other pharmaceutically acceptable salts and methods of preparing these salts may be found in, for example, Remington's Pharmaceutical Sciences (18$^{th}$ Edition, Mack Publishing Co.).

The invention also relates to any and all tautomeric forms of the compounds of formula I and the enantiomers of formula II.

Methods of Preparation

The present invention provides processes for preparing compounds and enantiomers of formula I and II, or salts thereof.

Throughout the following description of such processes it is to be understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis", T. W. Green, P. G. M. Wuts, Wiley-Interscience, New York, (1999). References and descriptions of other suitable reactions are described in textbooks of organic chemistry, for example, "Advanced Organic Chemistry", March, 4th ed. McGraw Hill (1992) or, "Organic Synthesis", Smith, McGraw Hill, (1994). For representative examples of heterocyclic chemistry see for example "Heterocyclic Chemistry", J. A. Joule, K. Mills, G. F. Smith, 3rd ed. Chapman and Hall (1995), p. 189-224 and "Heterocyclic Chemistry", T. L. Gilchrist, 2nd ed. Longman Scientific and Technical (1992), p. 248-282.

The term "room temperature" and "ambient temperature" shall mean, unless otherwise specified, a temperature between 16 and 25° C.

The term "elevated temperature" shall mean, unless otherwise specified, a temperature between 50 and 150° C.

Schemes

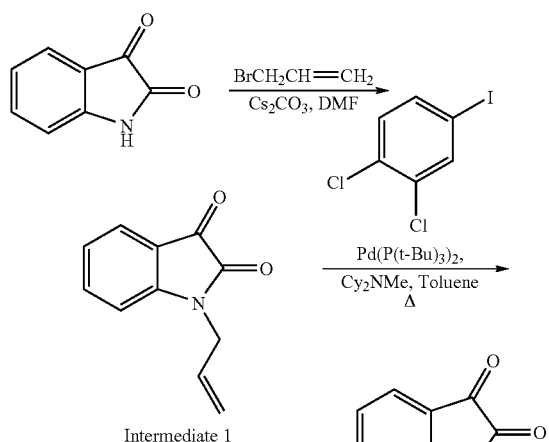

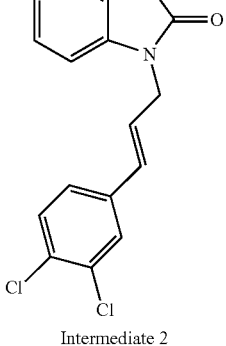

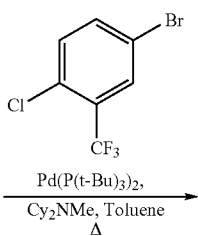

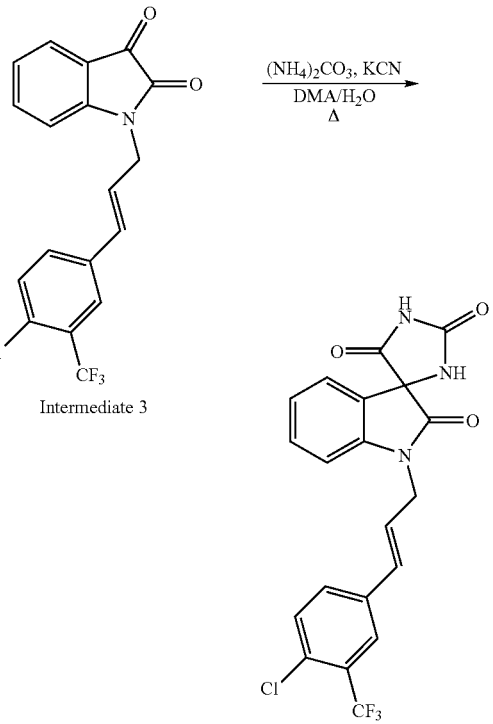

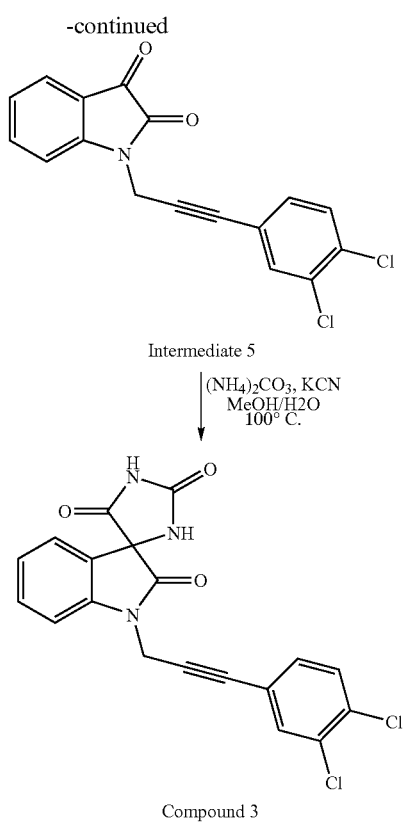

Intermediate 5

(NH4)2CO3, KCN
MeOH/H2O
100° C.

Compound 3

One embodiment of the invention relates to a process for the preparation of compounds of formula I, wherein $R^1$, $R^2$ and X are as defined as hereinabove, comprising:

Reaction of an Optionally Protected Compound of Formula III

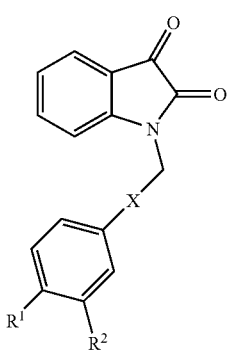

III i) with KCN and $(NH_4)_2CO_3$ in at elevated temperature in a suitable solvent, and thereafter optionally:

ii) converting the compound of the formula I into another compound of the formula I; and/or iii) removing any protecting groups; and/or iv) forming a pharmaceutically acceptable salt.

One embodiment of the invention relates to a process for the preparation of an enantiomer of formula II, wherein $R^1$, $R^2$ and X are as defined as hereinabove, comprising:

Reaction of an Optionally Protected Compound of Formula III

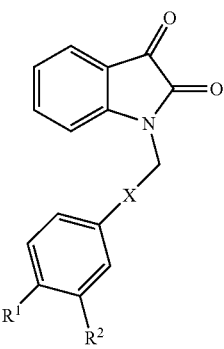

III i) with KCN and $(NH_4)_2CO_3$ in elevated temperature in a suitable solvent, and thereafter separation of said enantiomer from the racemic mixture by supercritical fluid chromatography.

Intermediates

A further embodiment of the invention relates to compounds selected from the group consisting of
1-Allyl-1H-indole-2,3-dione
1-[(2E)-3-(3,4-dichlorophenyl)prop-2-en-1-yl]-1H-indole-2,3-dione
1-{(2E)-3-[4-chloro-3-(trifluoromethyl)phenyl]prop-2-en-1-yl}-1H-indole-2,3-dione
1-prop-2-yn-1-yl-1H-indole-2,3-dione
1-[3-(3,4-dichlorophenyl)prop-2-yn-1-yl]-1H-indole-2,3-dione which may be used as intermediates in the preparation of compounds suited for the treatment of VR1 mediated disorders, especially for use as intermediates for the preparation of compounds of formula I and/or enantiomers of formula II.

One embodiment of the invention relates to a process for the preparation of intermediates of formula III, wherein $R^1$, $R^2$ and X are as defined as hereinabove, comprising:

Reaction of an Optionally Protected Compound of Formula IV

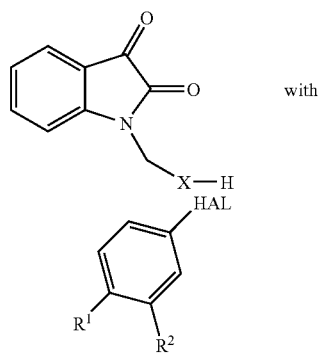

IV with where HAL is an halogen atom, in the presence of a suitable palladium catalyst, such as $Pd(P(t-Bu)_3)_2$ or $Pd(OAc)_2$, in a suitable solvent, and thereafter optionally:

ii) converting the intermediate of formula III into another intermediate of formula III; and/or iii) removing any protecting groups.

Pharmaceutical Composition

According to one embodiment of the present invention there is provided a pharmaceutical composition comprising as active ingredient a therapeutically effective amount of the compound of formula I and/or the enantiomer of formula II, or salts thereof, in association with one or more pharmaceutically acceptable diluents, excipients and/or inert carriers.

The composition may be in a form suitable for oral administration, for example as a tablet, pill, syrup, powder, granule or capsule, for parenteral injection (including intravenous, subcutaneous, intramuscular, intravascular or infusion) as a sterile solution, suspension or emulsion, for topical administration e.g. as an ointment, patch or cream, for rectal administration e.g. as a suppository or for inhalation.

In general the above compositions may be prepared in a conventional manner using one or more conventional excipients, pharmaceutical acceptable diluents and/or inert carriers. Suitable daily doses of the compounds of formula I and/or the enantiomer of formula II in the treatment of a mammal, including man, are approximately 0.01 to 250 mg/kg bodyweight at peroral administration and about 0.001 to 250 mg/kg bodyweight at parenteral administration.

The typical daily dose of the active ingredient varies within a wide range and will depend on various factors such as the relevant indication, severity of the illness being treated, the route of administration, the age, weight and sex of the patient and the particular compound being used, and may be determined by a physician.

Medical Use

The compounds according to the present invention are useful in therapy. The compounds and enantiomers of the invention, or salts thereof, as well as their corresponding active metabolites, exhibit a high degree of potency and selectivity for individual vanilloid receptor 1 (VR1) groups. Accordingly, the compounds of the present invention are expected to be useful in the treatment of conditions associated with excitatory activation of vanilloid receptor 1 (VR1).

The compounds may be used to produce an inhibitory effect of VR1 in mammals, including man.

VR1 are highly expressed in the peripheral nervous system and in other tissues. Thus, it is expected that the compounds and enantiomers of the invention are well suited for the treatment of VR1 mediated disorders.

The compounds and enantiomers of the invention are expected to be suitable for the treatment of acute and chronic pain, acute and chronic neuropathic pain and acute and chronic inflammatory pain.

Examples of such disorder may be selected from the group comprising low back pain, post-operative pain, visceral pains like chronic pelvic pain and the like.

The compounds of the invention are also expected to be suitable for the treatment of acute and chronic nociceptive pain.

Further relevant disorders may be selected from the group comprising cystitis, including interstitial cystitis and pain related thereto, ischeamic, sciatia, multiple sclerosis, arthritis, osteoarthritis, rheumatoid arthritis, fibromyalgia, pain and other signs and symptoms associated with psoriasis, pain and other signs and symptoms associated with cancer, emesis, urinary incontinence, hyperactive bladder and HIV neuropathy.

Additional relevant disorders may be selected from the group comprising gastro-esophageal reflux disease (GERD), irritable bowel syndrome (IBS), inflammatory bowel disease (IBD) and pancreatitis.

Other relevant disorders are related to respiratory diseases and may be selected from the group comprising asthma, cough, chronic obstructive lung disease, specifically chronic obstructive pulmonary disease (COPD) and emphysema, lung fibrosis and interstitial lung disease.

Yet other relevant disorders are obesity and obesity-related diseases or disorders, and migraine.

In one embodiment the obesity or obesity-related diseases or disorders is selected from the following: cardiovascular disease, hypertension, cancer and reproductive disorders.

The VR1 inhibitor(s) may be administrated by either an oral or inhaled route. The respiratory disease may be an acute and chronic illness and may be related to infection(s) and/or exposure to environmental pollution and/or irritants.

The compounds and enantiomers of the invention may also be used as antitoxin to treat (over-) exposure to VR1 activators like capsaicin, tear gas, acids or heat. Regarding heat, there is a potential use for VR1 antagonists in (sun-) burn induced pain, or inflammatory pain resulting from burn injuries.

The compounds may further be used for treatment of tolerance to VR1 activators. One embodiment of the invention relates to the compounds and enantiomers of the invention as hereinbefore defined, for use as medicaments.

Another embodiment of the invention relates to the compounds and enantiomers of the invention as hereinbefore defined, for use as medicaments for treatment of VR1 mediated disorders.

A further embodiment of the invention relates to the compounds and enantiomers of the invention as hereinbefore defined, for use as medicaments for treatment of acute and chronic pain disorders.

Another embodiment of the invention relates to the compounds and enantiomers of the invention as hereinbefore defined for use as medicaments for treatment of acute and chronic nociceptive pain.

Yet another embodiment of the invention relates to the compounds and enantiomers of the invention as hereinbefore defined, for use as medicaments for treatment of acute and chronic neuropathic pain.

Yet a further embodiment of the invention relates to the compounds and enantiomers of the invention as hereinbefore defined, for use as medicaments for treatment of acute and chronic inflammatory pain.

One embodiment of the invention relates to the compounds and enantiomers of the invention as hereinbefore defined, for use as medicaments for treatment of low back pain, post-operative pain and visceral pains like chronic pelvic pain.

Another embodiment of the invention relates to the compounds and enantiomers of the invention as hereinbefore defined, for use as medicaments for treatment of cystitis, including interstitial cystitis and pain related thereto, ischeamic, sciatia, multiple sclerosis, arthritis, osteoarthritis, rheumatoid arthritis, fibromyalgia, pain and other signs and symptoms associated with psoriasis, pain and other signs and symptoms associated with cancer, emesis, urinary incontinence, hyperactive bladder and HIV neuropathy.

A further embodiment of the invention relates to the compounds and enantiomers of the invention as hereinbefore defined, for use as medicaments for treatment of gastro-esophageal reflux disease (GERD), irritable bowel syndrome (IBS), inflammatory bowel disease (IBD) and pancreatitis.

Yet a further embodiment of the invention relates to the compounds and enantiomers of the invention as hereinbefore defined, for use as medicaments for treatment of respiratory diseases selected from the group comprising asthma, cough, chronic obstructive pulmonary disease (COPD), chronic obstructive lung disease and emphysema, lung fibrosis and interstitial lung disease.

One embodiment of the invention relates to the use of the compounds and enantiomers of the invention as hereinbefore defined, in the manufacture of medicaments for treatment of VR1 mediated disorders and for treatment of acute and chronic pain disorders, acute and chronic neuropathic pain and acute and chronic inflammatory pain, and respiratory diseases and any other disorder mentioned above.

Another embodiment of the invention relates to a method of treatment of VR1 mediated disorders and acute and chronic pain disorders, acute and chronic neuropathic pain and acute and chronic inflammatory pain, and respiratory diseases, and any other disorder mentioned above, comprising administering to a mammal, including man in need of such treatment, a therapeutically effective amount of a compound and/or enantiomer of the invention, as hereinbefore defined.

A further embodiment of the invention relates to a pharmaceutical composition comprising a compound and/or enantiomer of the invention as hereinbefore defined, for use in treatment of VR1 mediated disorders and for treatment of acute and chronic pain disorders, acute and chronic neuropathic pain and acute and chronic inflammatory pain, and respiratory diseases, and any other disorder mentioned above.

In the context of the present specification, the term "therapy" and "treatment" includes prevention and prophylaxis, unless there are specific indications to the contrary. The terms "treat", "therapeutic" and "therapeutically" should be construed accordingly.

In this specification, unless stated otherwise, the term "inhibitor" and "antagonist" mean a compound that by any means, partly or completely, blocks the transduction pathway leading to the production of a response by the ligand.

The term "disorder", unless stated otherwise, means any condition and disease associated with vanilloid receptor activity.

Non-Medical Use

In addition to their use in therapeutic medicine, the compounds and enantiomers of the invention, or salts thereof, are also useful as pharmacological tools in the development and standardisation of in vitro and in vivo test systems for the evaluation of the effects of inhibitors of VR1 related activity in laboratory animals such as cats, dogs, rabbits, monkeys, rats and mice, as part of the search for new therapeutics agents.

EXAMPLES

The invention will now be illustrated by the following non-limiting examples.

General Methods

The invention will now be illustrated by the following Examples in which, generally:

(i) operations were carried out at ambient or room temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) The $^1$H NMR spectra were recorded on Bruker at 400 MHz. The mass spectra were recorded utilising electrospray (LC-MS; LC:Waters 2790, column XTerra MS $C_8$ 2.5 μm 2.1×30 mm, buffer gradient $H_2O$+0.1% TFA:$CH_3CN$+0.04% TFA, MS: micromass ZMD//ammonium acetate buffer) ionisation techniques;

(iv) yields, where present, are not necessarily the maximum attainable;

(v) the following abbreviations have been used:

| | |
|---|---|
| alloc | allyloxycarbonyl |
| DCE | dichloroethane |
| DCM | dichloromethane |
| DMAP | dimethylaminopyridine |
| EDC | 1-(3-dimethylaminopropyl)-3-ethylcarbodiimide hydrochloride |
| HATU | O-(7-azabenzotriazol-1-yl)-N,N,N',N'-tetramethyluronium hexafluorophosphate |
| HPLC | high performance liquid chromatography |
| LC | liquid chromatography |
| MsCl | methanesulfonyl chloride |
| MS | mass spectrometry |
| ret. time | retention time |
| TFA | trifluroacetic acid |
| THF | tetrahydrofurane |
| DMF | dimethyformamide |
| TMEDA | tetramethylethylenediamine |
| EtOAc | ethyl acetate |
| BuLi | Butyl lithium |
| TMEDA | tetramethylethylenediamine |

Intermediate 1: 1-Allyl-1H-indole-2,3-dione

Isatin (10.102 g, 68.7 mmol) was dissolved in 100 mL dry DMF, and $Cs_2CO_3$ (24.609 g, 75.5 mmol) was added. To the resulting purple-brown suspension was added allyl bromide (7.2 mL, 83 mmol) and the reaction was stirred at room temperature for 16 h. The resulting cloudy orange-brown mixture was concentrated in vacuo, and the residue was partitioned between EtOAc (160 mL) and water (80 mL). The layers were separated, and the aqueous layer was extracted with additional EtOAc (2×80 mL). The combined organic phases were dried over $Na_2SO_4$, filtered, and concentrated in vacuo. To the residue was added 300 mL hexanes. The mixture was heated to 70° C. with a water bath, and EtOAc was added until the compound went into solution (approx. 80 mL EtOAc). A small amount of insoluble red material was removed, and then the solution was allowed to cool. The resulting red crystals were filtered, washed with 3×30 mL hexanes, and then dried under vacuum to provide the title compound (11.740 g, 91%). $^1$H NMR (600 MHz, CHLOROFORM-D) δ ppm 4.36 (d, J=5.6 Hz, 2H), 5.26-5.34 (m, 2H), 5.78-5.88 (m, 1H), 6.88 (d, J=7.9 Hz, 1H), 7.11 (t, J=7.6 Hz, 1H), 7.56 (td, J=7.8, 1.3 Hz, 1H), 7.61 (d, J=7.4 Hz, 1H). MS (ESI) (M+H)$^+$=188.

Intermediate 2: 1-[(2E)-3-(3,4-dichlorophenyl)prop-2-en-1-yl]-1H-indole-2,3-dione A mixture of 1-allyl-1H-indole-2,3-dione (1.00 g, 5.34 mmol), Pd(P(t-Bu)$_3$)$_2$ (0.0819 g, 0.16 mmol), 1,2-dichloro-4-iodobenzene (1.458 g, 5.34 mmol), dry toluene (10 mL), and N-cyclohexyl-N-methylcyclohexanamine (1.23 mL, 5.86 mmol) in an oven-dried sealed tube under an atmosphere of $N_2$ was heated for 16 h at 80° C. The reaction was cooled, diluted with $CH_2Cl_2$, and loaded directly onto a silica gel column that had been packed with $CH_2Cl_2$. The column was eluted with a gradient of 100% $CH_2Cl_2$ to 95:5 $CH_2Cl_2$:

EtOAc. The appropriate fractions were combined to provide the title compound as an orange solid (1.489 g, 84%). $^1$H NMR (600 MHz, CHLOROFORM-D) δ ppm 4.52 (d, J=5.9 Hz, 2H), 6.19 (dt, J=15.9, 5.9 Hz, 1H), 6.56 (d, J=15.6 Hz, 1H), 6.91 (d, J=7.9 Hz, 1H), 7.09-7.20 (m, 2H), 7.37 (d, J=8.2 Hz, 1H), 7.42 (s, 1H), 7.57 (t, J=7.8 Hz, 1H), 7.64 (d, J=7.4 Hz, 1H).

Intermediate 3: 1-{(2E)-3-[4-chloro-3-(trifluoromethyl)phenyl]prop-2-en-1-yl}-1H-indole-2,3-dione Six separate oven-dried sealed tubes were charged with 1-allyl-1H-indole-2,3-dione (0.100 g, 0.534 mmol), Pd(P(t-Bu)$_3$)$_2$ (0.0082 g, 0.016 mmol), 4-bromo-1-chloro-2-(trifluoro-methyl)benzene (0.139 g, 0.536 mmol), dry toluene (1 mL), and N-cyclohexyl-N-methyl-cyclohexanamine (0.12 mL, 0.57 mmol) under an atmosphere of N$_2$. The tubes were heated for 16 h at 80° C. in an oil bath, and then the reactions were cooled and concentrated in vacuo. The crude material was used in the subsequent step.

Intermediate 4:
1-prop-2-yn-1-yl-1H-indole-2,3-dione

To a solution of isatin (200 mg, 1.36 mmol) in DMF (5 mL) was added cesium carbonate (487 mg, 1.5 mmol). The reaction was stirred at room temperature for 90 minutes. Propargyl bromide (243 uL, 1.63 mmol) was then added. The reaction was stirred overnight at room temperature, concentrated in vacuo, dissolved in EtOAc and washed with saturated NaHCO$_{3(aq)}$ (1×). The layers were separated and the aqueous layer was extracted with additional EtOAc (2×). The combined organic phases was dried over Na$_2$SO$_4$, filtered and concentrated in vacuo. Further purification of the residue was not necessary. The title compound was obtained as an orange solid (255 mg, quantitative yield). $^1$H NMR (400 MHz, CDCl$_3$) δ 2.31 (t, J=2.54 Hz, 1H), 4.55 (d, J=2.54 Hz, 2H), 7.12-7.15 (m, 1H), 7.19 (dt, J=7.52, 0.78 Hz, 1H), 7.63-7.68 (m, 2H).

Intermediate 5: 1-[3-(3,4-dichlorophenyl)prop-2-yn-1-yl]-1H-indole-2,3-dione

To a mixture of 1-prop-2-yn-1-yl-1H-indole-2,3-dione (190 mg, 1.03 mmol), 1,2-dichloro-4-iodobenzene (420 mg, 1.54 mmol), copper(I) iodide (11.0 mg, 0.06 mmol) and triphenylphosphine (40.0 mg, 0.15 mmol) in degassed DMF (24 mL) was added triethyl-amine (307 μL, 2.15 mmol). The reaction was stirred for 5 minutes and Pd(OAc)$_2$ (13.0 mg, 0.06 mmol) was then added. The reaction was stirred at room temperature for 2 days, concentrated in vacuo, dissolved in EtOAc and washed with saturated NaHCO$_{3(aq)}$ (1×). The layers were separated and the aqueous layer was extracted with additional EtOAc (2×).

The combined organic phases was dried over Na$_2$SO$_4$, filtered and concentrated in vacuo. The crude product was purified by silica gel column chromatography, eluting with a solvent gradient of 35% EtOAc/Hexanes to 75% EtOAc/Hexanes, to give the title compound as an orange solid with 90% purity (375 mg, quantitative yield). $^1$H NMR (400 MHz, DMSO-D$_6$) δ 4.82 (s, 2H), 7.18 (dt, J=7.52, 0.78 Hz, 1H), 7.32 (d, J=8.01 Hz, 1H), 7.41 (dd, J=8.40, 1.95 Hz, 1H), 7.60 (dd, J=7.42, 0.78 Hz, 1H), 7.63 (d, J=8.40 Hz, 1H), 7.70-7.75 (m, 2H).

Compound 1: 1'-[(2E)-3-(3,4-dichlorophenyl)prop-2-en-1-yl]-2H,5H-spiro[imidazolidine-4,3'-indole]-2,2',5(1'H)-trione Four identical reactions were set up. For each reaction, 1-[(2E)-3-(3,4-dichloro-phenyl)prop-2-en-1-yl]-1H-indole-2,3-dione (200 mg, 0.602 mmol) was dissolved in 5 mL N,N-dimethylacetamide (5 mL) in a sealed tube. Ammonium carbonate (0.555 g, 5.78 mmol) was added, followed by a solution of KCN (0.0470 g, 0.722 mmol) in water (5 mL). The tubes were sealed and then heated to 100° C. in an oil bath for 2 h. The reactions turned from red to deep purple to yellow over the course of the reaction. The reactions were cooled and then concentrated in vacuo. Each reaction was taken up in EtOAc (5 mL) and water (5 mL). All 4 reactions were passed through one Varian ChemElut CE1020 column, and the column was rinsed with additional EtOAc (2×20 mL). The organic extracts were concentrated in vacuo, and the residue purified by silica gel column chromatography (1:2 Hexanes:EtOAc) to give the title compound (0.7075 g, 73%) as a white solid. $^1$H NMR (400 MHz, METHANOL-D$_4$) δ ppm 4.45-4.53 (m, 1H), 4.57-4.66 (m, 1H), 6.35 (dt, J=16.1, 5.1 Hz, 1H), 6.59 (dt, J=16.2, 1.5 Hz, 1H), 7.08 (d, J=7.8 Hz, 1H), 7.17 (td, J=7.6, 0.9 Hz, 1H), 7.30 (dd, J=8.4, 2.0 Hz, 1H), 7.37 (dd, J=7.4, 1.0 Hz, 1H), 7.39-7.45 (m, 2H), 7.53 (d, J=2.1 Hz, 1H). MS (APPI) (M+H)$^+$=402. Anal. Calcd for $C_{19}H_{13}Cl_2N_3O_3$: C, 56.74; H, 3.26; N, 10.45. Found: C, 56.64; H, 3.26; N, 10.27.

The individual enantiomers of 1'-[(2E)-3-(3,4-dichlorophenyl)prop-2-en-1-yl]-2H,5H-spiro[imidazolidine-4,3'-indole]-2,2',5(1'H)-trione were obtained through separation of the racemic mixture (214 mg) by supercritical fluid chromatography (SFC) on a chiral solid support using a Berger SFC Multigram II system (Mettler Toledo) (SFC conditions: 50% Ethanol/CO$_2$ eluent, CHIRALCEL® OD SFC column (Chiral Technologies), 21×250 mm, 10 micron, flow 50 mL/min. Variable wavelength UV detector 254 or 280 nm, 6 minute run.) Enantiomeric purities were determined by SFC on a chiral solid support using a Berger SFC Analytix/MS system (Mettler Toledo) (SFC conditions: 50% Ethanol/CO$_2$ eluent, CHIRALCEL® OD SFC column (Chiral Technologies), 4.6×250 mm, 5 micron, flow 2.2 mL/min. Diode array UV, MS detector, 6 minute run). Yield: 80.7 mg (38%) of the first eluting enantiomer, 80.0 mg (37%) of the second eluting enantiomer. The IUPAC names of the enantiomers were generated using software ACD/Name (ACD/Labs 7.00 Release Product version: 7.07, build: 16 Jul. 2003).

Enantiomer 1A: (4S)-1'-[(2E)-3-(3,4-dichlorophenyl)prop-2-en-1-yl]-2H,5H-spiro[imidazolidine-4,3'-indole]-2,2',5(1'H)-trione First eluting enantiomer: Retention time=2.46 min, e.e.>99%, $[α]_D^{22}$=+16.8 (c 0.959 g/100 mL, CD$_3$OD), $^1$H NMR (400 MHz, METHANOL-D$_4$) δ ppm 4.44-4.53 (m, 1H), 4.57-4.65 (m, 1H), 6.35 (dt, J=16.1, 4.9 Hz, 1H), 6.58 (dt, J=16.0, 1.6 Hz, 1H), 7.08 (d, J=7.8 Hz, 1H), 7.17 (td, J=7.6, 0.9 Hz, 1H), 7.30 (dd, J=8.4, 2.0 Hz, 1H), 7.35-7.39 (m, 1H), 7.38-7.45 (m, 2H), 7.52 (d, J=2.0 Hz, 1H). MS (APPI) (M+H)$^+$=402.

The absolute configuration of this enantiomer is determined by X-ray crystallography.

Enantiomer 1B: (4R)-1'-[(2E)-3-(3,4-dichlorophenyl)prop-2-en-1-yl]-2H,5H-spiro[imidazolidine-4,3'-indole]-2,2',5(1'H)-trione Second eluting enantiomer: Retention time=4.21 min, e.e.>99%, [α]$_D^{22}$=−15.0 (c 0.908 g/100 mL, CD$_3$OD), $^1$H NMR (400 MHz, METHANOL-D$_4$) δ ppm 4.44-4.53 (m, 1H), 4.56-4.65 (m, 1H), 6.35 (dt, J=16.0, 5.1 Hz, 1H), 6.58 (dt, J=16.1, 1.5 Hz, 1H), 7.08 (d, J=7.8 Hz, 1H), 7.17 (td, J=7.6, 0.9 Hz, 1H), 7.30 (dd, J=8.5, 2.1 Hz, 1H), 7.35-7.39 (m, 1H), 7.39-7.45 (m, 2H), 7.52 (d, J=2.0 Hz, 1H). MS (APPI) (M+H)$^+$=402.

The absolute configuration of this enantiomer was determined by X-ray crystallography.

Compound 2: 1'-{(2E)-3-[4-chloro-3-(trifluoromethyl)phenyl]prop-2-en-1-yl}-2H,5H-spiro[imidazolidine-4,3'-indole]-2,2',5(1'H)-trione Six tubes of crude 1-{(2E)-3-[4-chloro-3-(trifluoromethyl)phenyl]prop-2-en-1-yl}-H-indole-2,3-dione were treated identically. The material in each tube was dissolved in N,N-dimethylacetamide (4.4 mL). Ammonium carbonate (0.493 g, 5.13 mmol) was added to each tube, followed by a solution of KCN (0.0417 g, 0.640 mmol) in water (4.4 mL). The tubes were sealed and then heated to 100° C. in an oil bath for 3 h. The reactions were cooled and then concentrated in vacuo. Each reaction was taken up in EtOAc (8 mL) and water (5 mL), and then passed through a Varian ChemElut CE1005 column. The columns were rinsed with additional EtOAc (2×8 mL) and the organic extracts were concentrated in vacuo. The residue was purified by reverse phase preparative scale LC/MS to give the title compound (0.2834 g, 20% over 2 steps) as a slightly orange solid following lyophilization. $^1$H NMR (400 MHz, DMSO-D$_6$) δ ppm 4.48-4.59 (m, 2H), 6.52 (dt, J=16.2, 4.8 Hz, 1H), 6.58-6.65 (m, 1H), 7.10-7.18 (m, 2H), 7.38-7.45 (m, 2H), 7.64-7.68 (m, 1H), 7.71-7.81 (m, 2H), 8.68 (d, J=1.0 Hz, 1H), 11.43 (s, 1H). MS (APPI) (M+H)$^+$=436.

The individual enantiomers of 1'-{(2E-3-[4-chloro-3-(trifluoromethyl)phenyl]prop-2-en-1-yl}-2H,5H-spiro[imidazolidine-4,3'-indole]-2,2',5(1'H)-trione were obtained through separation of the racemic mixture (19.96 g) by supercritical fluid chromatography (SFC) on a chiral solid support using a Novasep SFC SuperSep 50 system (Novasep, Inc.) (SFC conditions: 30% Methanol/CO$_2$ eluent, CHIRALCEL® OD-H SFC column (Chiral Technologies, Inc), 3×25 cm, 5 micron, flow rate 150 mL/min. Variable wavelength UV detector 230 nm, 5 minute run.) Enantiomeric purities were determined by SFC on a chiral solid support using a Berger SFC system (Mettler Toledo) (SFC conditions: 30% Methanol/CO$_2$ eluent, CHIRALCEL® OD-H SFC column (Chiral Technologies, Inc), 4.6×250 mm, 5 micron, flow rate 2 mL/min. Variable wavelength UV detector 220 nm, 9 minute run.) Yield: 45% of the first eluting enantiomer and 42% of the second eluting enantiomer. The IUPAC names of the enantiomers were generated using software ACD/Name (ACD/Labs 7.00 Release Product version: 7.07, build: 16 Jul. 2003).

Enantiomer 2A: (4S)-1'-{(2E)-3-[4-chloro-3-(trifluoromethyl)phenyl]prop-2-en-1-yl}-2H,5H-spiro[imidazolidine-4,3'-indole]-2,2',5(1'H)-trione First eluting enantiomer: Retention time=4.29 min, e.e.>99%, [α]$_D^{22}$=+16.8 (c 1.03 g/100 mL, CD$_3$OD), $^1$H NMR (400 MHz, DMSO-D$_6$) δ ppm 4.53 (d, J=4.5 Hz, 2H), 6.52 (dt, J=16.2, 4.8 Hz, 1H), 6.58-6.67 (m, 1H), 7.09-7.19 (m, 2H), 7.37-7.46 (m, 2H), 7.63-7.69 (m, 1H), 7.71-7.76 (m, 1H), 7.79 (d, J=2.0 Hz, 1H), 8.68 (d, J=1.4 Hz, 1H), 11.43 (s, 1H). MS (APPI) (M+H)$^+$=436.

The absolute configuration of this enantiomer is determined by X-ray crystallography.

Enantiomer 2B: (4R)-1'-{(2E)-3-[4-chloro-3-(trifluoromethyl)phenyl]prop-2-en-1-yl}-2H,5H-spiro[imidazolidine-4,3'-indole]-2,2',5(1'H)-trione Second eluting enantiomer: Retention time=5.92 min, e.e.>98%, [α]$_D^{22}$=−15.6 (c 1.33 g/100 mL, CD$_3$OD), $^1$H NMR (400 MHz, DMSO-D$_6$) δ ppm 4.53 (d, J=4.5 Hz, 2H), 6.52 (dt, J=16.2, 4.8 Hz, 1H), 6.58-6.66 (m, 1H), 7.09-7.19 (m, 2H), 7.37-7.46 (m, 2H), 7.63-7.68 (m, 1H), 7.70-7.76 (m, 1H), 7.79 (d, J=2.0 Hz, 1H), 8.68 (d, J=1.4 Hz, 1H), 11.43 (s, 1H). MS (APPI) (M+H)$^+$=436.

The absolute configuration of this enantiomer is determined by X-ray crystallography.

Compound 3: 1'-[3-(3,4-dichlorophenyl)prop-2-yn-1-yl]-2H,5H-spiro[imidazolidine-4,3'-indole]-2,2',5(1'H)-trione A mixture of Intermediate 5 (50 mg, 0.15 mmol), potassium cyanide (12 mg, 0.18 mmol), and ammonium carbonate (140 mg, 1.45 mmol) in 1:1 MeOH:H$_2$O (2.5 mL) was heated at 100° C. for 6 hours. The reaction was then cooled, concentrated in vacuo to remove the MeOH, diluted with EtOAc and washed with H$_2$O (1×). The layers were separated and the aqueous layer was extracted with additional EtOAc (3×). The combined organic phases were dried over Na$_2$SO$_4$, filtered and concentrated in vacuo. The residue was purified by reverse phase HPLC (gradient 50-80% CH$_3$CN in H$_2$O containing 0.1% trifluoroacetic acid) to give the title compound (2 mg, 3% yield) as its TFA salt. This material was lyophilized from CH$_3$CN/H$_2$O to produce a pale yellow solid. Purity (HPLC): 95% (215 nm), 94% (254 nm); $^1$H NMR (400 MHz, DMSO-D$_6$) δ ppm 4.82-4.93 (m, 2H), 7.17 (dt, J=7.57, 0.88 Hz, 1H), 7.32 (d, J=7.81 Hz, 1H), 7.40 (dd, J=8.30, 2.05 Hz, 1H), 7.44 (dd, J=7.42, 0.78 Hz, 1H), 7.49 (dt, J=7.76, 1.27 Hz, 1H), 7.64 (d, J=8.20 Hz, 1H), 7.70 (d, J=1.95 Hz, 1H), 8.69 (d, J=1.56 Hz, 1H), 11.42 (s, 1H). Found: C, 57.05; H, 2.75; N, 10.55. C$_{19}$H$_{11}$N$_3$O$_3$Cl$_2$ has C, 57.02; H, 2.77; N, 10.50%.

The individual enantiomers of 1'-[3-(3,4-dichlorophenyl)prop-2-yn-1-yl]-2H,5H-spiro[imidazolidine-4,3'-indole]-2,2',5(1'H)-trione were obtained through separation of the racemic mixture (200 mg) by supercritical fluid chromatography (SFC) on a chiral solid support using SFC Multigram II system (Mettler Toledo) (SFC conditions: 50% Ethanol/CO$_2$ eluent, ChiralCel OD SFC column (Chiral Technologies), 21×250 mm, 10 micron, flow 50 mL/min. Variable wavelength UV detector 254 or 280 nm, 6 minute run.) Enantiomeric purities were determined by SFC on a chiral solid support using a Berger SFC Analytix/MS system (Mettler Toledo) (SFC conditions: 50% Ethanol/CO$_2$ eluent, ChiralCel OD SFC column (Chiral Technologies), 4.6×250 mm, 5 micron, flow 2.2 mL/min. Diode array UV, MS detector, 6 minute run). Yield: 83 mg (42%) of the first eluting enantiomer, 82 mg (41%) of the second eluting enantiomer. The IUPAC names of the enantiomers were generated using software ACD/Name (ACD/Labs 7.00 Release Product version: 7.07, build: 16 Jul. 2003).

Enantiomer 3A: (4S)-1'-[3-(3,4-dichlorophenyl)prop-2-yn-1-yl]-2H,5H-spiro[imidazolidine-4,3'-indole]-2,2',5(1'H)-trione First eluting enantiomer: Retention time=3.19 min, e.e.>99%, $[\alpha]_D^{22}$=+72.8 (c 1.00 g/100 mL, CD$_3$OD), $^1$H NMR (400 MHz, CD$_3$OD) δ ppm 4.74-4.88 (m, 2H), 7.20 (dt, J=7.57, 0.88 Hz, 1H), 7.26-7.31 (m, 2H), 7.36 (dd, J=7.52, 0.68 Hz, 1H), 7.45-7.51 (m, 2H), 7.55 (d, J=1.76 Hz, 1H). MS (APPI) (M+H)$^+$=400.

The absolute configuration of this enantiomer is determined by X-ray crystallography.

Enantiomer 3B: (4R)-1'-[3-(3,4-dichlorophenyl)prop-2-yn-1-yl]-2H,5H-spiro[imidazolidine-4,3'-indole]-2,2',5(1'H)-trione Second eluting enantiomer: Retention time=4.47 min, e.e.>99%, $[\alpha]_D^{22}$=-75.1 (c 1.03 g/100 mL, CD$_3$OD), $^1$H NMR (400 MHz, CD$_3$OD) δ ppm 4.74-4.87 (m, 2H), 7.17-7.22 (m, 1H), 7.26-7.31 (m, 2H), 7.35-7.38 (m, 1H), 7.44-7.51 (m, 2H), 7.54 (d, J=1.76 Hz, 1H). MS (APPI) (M+H)$^+$=400.

The absolute configuration of this enantiomer is determined by X-ray crystallography.

Pharmacology hVR1FLIPR (Fluorometric Image Plate Reader) Screening Assay

Transfected CHO cells, stably expressing hVR1 (15,000 cells/well) are seeded in 50 µL media in a black clear bottom 384 plate (Greiner) and grown in a humidified incubator (37° C., 2% CO$_2$), 24-30 hours prior to experiment.

Subsequently, the media is removed from the cell plate by inversion and 2 µM Fluo-4 is added using a multidrop (Labsystems). Following the 40 min dye incubation in the dark at 37° C. and 2% CO$_2$, the extracellular dye present is washed away using an EMBLA (Scatron), leaving the cells in 40 µL of assay buffer (1×HBSS, 10 mM D-Glucose, 1 mM CaCl$_2$, 10 mM HEPES, 10×7.5% NaHCO$_3$ and 2.5 mM Probenecid).

FLIPR Assay—IC$_{50}$ Determination Protocol

For IC$_{50}$ determinations the fluorescence is read using FLIPR filter 1 (em 520-545 nM). A cellular baseline recording is taken for 30 seconds, followed by a 20 µL addition of 10, titrated half-log concentrations of the test compound, yielding cellular concentration ranging from 3 µM to 0.1 nM. Data is collected every 2 seconds for a further 5 min prior to the addition of a VR1 agonist solution: either 50 nM solution of capsaicin or MES (2-[N-morpholino]ethanesulfonic acid) buffer (pH 5.2), by the FLIPR pipettor. The FLIPR continues to collect data for a further 4 min. Compounds having antagonistic properties against the hVR1 will inhibit the increase in intracellular calcium in response to the capsaicin addition. This consequently leading to a reduction in fluorescence signal and providing a reduced fluorescence reading, compared with no compound, buffer controls. Data is exported by the FLIPR program as a sum of fluorescence calculated under the curve upon the addition of capsaicin. Maximum inhibition, Hill slope and IC$_{50}$ data for each compound are generated.

A comparative aldose reductase activity determination was carried out by the company MDS Pharma Services—Taiwan Ltd; the results of that study is set forth in Table 1 below.

| List of abbreviations | |
| --- | --- |
| VR1 | vanilloid receptor 1 |
| IBS | irritable bowel syndrome |
| IBD | inflammatory bowel disease |
| GERD | gastro-esophageal reflux disease |
| HEPES | 4-(2-Hydroxyethyl)piperazine-1-ethanesulfonic acid |

Results

Typical IC$_{50}$ values as measured in the assays described above are 10 µM or less. In one aspect of the invention the IC$_{50}$ is below 3000 nM. In another aspect of the invention the IC$_{50}$ is below 1000 nM.

TABLE 1

Results from the hVR1 FLIPR and a comparative aldose reductase activity determination

| Example No. | IC$_{50}$(human VR1, capsaicin) nM | IC$_{50}$(aldose reductase) nM |
| --- | --- | --- |
| Enantiomer 1A | 10000 nM | 25 nM |
| Enantiomer 1B | 43 nM | 758 nM |
| Enantiomer 2A | 3850 nM | 33 nM |
| Enantiomer 2B | 241 nM | 3300 nM |
| Enantiomer 3A | 15454 nM | 72.3 nM |
| Enantiomer 3B | 881 nM | 983 nM |

Biological Tests

The in vivo pharmacological properties of the present invention have been determined using two classical NSAID-sensitive inflammatory models, the Carrageenan model and the Freund's Complete Adjuvant (FCA) model.

In the former, Carrageenan-lambda (algae-derived polysaccharide, type IV, 100 µl, from Sigma-Aldrich), dissolved in sterile saline 0.9% at a concentration of 1%, and in the latter FCA (25 µl, from Sigma-Aldrich, (1 ml of FCA contains 1 mg *mycobacterium tuberculosis* heat killed and dried, 0.85 ml mineral oil and 0.15 ml mannide monooleate, cf. Nagakura et al. in *Journal of Pharmacology and Experimental Therapeutics*, 2003; 306(2):490-497)) is injected into the subcutaneous space under the plantar surface (intra-plantar; i.pl.) of the rat left hind paw. This creates an inflammatory response, with accompanying edema, redness, and hyperalgesia. Heat (and mechanical) hyperalgesia is fully developed by 3 hours for carrageenan, and remains stable for 6 hours, while FCA is fully developed by 24 h and remains stable for weeks. In order to assess the degree of hyperalgesia, the heat plantar test was chosen, as it is a robust, consistent, and reproducible endpoint (based on the Hargreaves method of assessing nociception, cf. *Pain*, 1988; 32(1):77-88). Rats are placed in individual plexiglass boxes on a glass surface, which is maintained at 30° C., and a heat-source (rate of heat increase: ~1.1° C./s) is focused onto the plantar surface of the affected paw. The time from the initiation of the heat until the animal withdraws the paw is recorded. A decrease in Paw Withdrawal Latency (PWL) relative to naïve animals indicates a hyperalgesic state.

The degree of reversal of hyperalgesia is measured by the ability of the compound to return PWL to normal levels. (4R)-1'-[(2E)-3-(3,4-dichlorophenyl)prop-2-en-1-yl]-2H, 5H-spiro[imidazolidine-4,3'-indole]-2,2',5(1'H)-trione (=Enantiomer 1B) was orally administered during the established phase of inflammation and tested at its Tmax. The PWL of each animal is measured twice, and the average of the two is taken as the response. The responses of all animals within a given group are then averaged, and Standard Deviation and Standard Error of the Mean (SEM) are calculated for each group. The data is expressed as mean±SEM. Statistical significance is assessed with a T-test for comparison between naïve and treated groups, and One Way ANOVA followed by Holm-Sidak multiple comparisons versus control (vehicle) group test for drug effectiveness. The level of statistical significance is set at $p<0.05$. GraphPad Prism® version 4 is used for non-linear regression analysis (using the variable slope sigmoidal equation model) of raw data to calculate the ED50, EC50, EC80, and Emax.

Prior to any manipulation, rats (150-175 g, Charles River, St. Constant, Canada) were housed in groups of 7-9 in a temperature controlled room (22±1.5° C., 30-80% humidity, 12 h light/dark cycle) and were acclimatized in the animal facility for at least one day prior to use. All experimental protocols are approved by the AstraZeneca Animal Care Committee. Experiments are performed during the light phase of the cycle, rooms are illuminated at 300 lux intensity. Animals have food and water ad libitum.

In vivo efficacy and potency of the tested compound in nociceptive pain are summarized in Table 2 below. The tested compound is potent and effective in reversing both carrageenan- and FCA-induced heat hyperalgesia.

TABLE 2

Efficacy and Potency in the carrageenan and FCA model in vivo
Compound tested: (4R)-1'-[(2E)-3-(3,4-dichlorophenyl)prop-2-en-1-yl]-2H,5H-spiro[imidazolidine-4,3'-indole]-2,2',5(1'H)-trione

|  | Carrageenan model | FCA model |
|---|---|---|
| ED50 (μmol/kg) | 10.6 | 52.8 |
| EC50 (μM) | 4.8 | 24 |
| Emax observed (%) | 76 | 100 |
| Extrapolated Emax (%) | 88 | >100 |
| EC80 (μM) | 10.7 | 100 |

What is claimed is:

1. A method of treating pain which comprises administering to a subject in need thereof an effective amount of (4R)-1'-[(2E)-3-(3,4-dichlorophenyl)prop-2-en-1-yl]-2H,5H-spiro[imidazolidine-4,3"-indole]-2,2'%5 (1'H)-trione or a pharmaceutically acceptable salt thereof.

* * * * *